United States Patent
Lei et al.

(10) Patent No.: US 9,346,724 B2
(45) Date of Patent: May 24, 2016

(54) METHOD FOR PREPARING 2,3,3,3-TETRAFLUOROPROPENE

(71) Applicant: Zhejiang Quhua Fluor-Chemistry Co., Ltd., Quzhou (CN)

(72) Inventors: Jun Lei, Ningbo (CN); Bo Yang, Quzhou (CN); Yan Zhang, Quzhou (CN); Yang Zhao, Quzhou (CN); Huadong Zhou, Quzhou (CN); Qiang Zhou, Quzhou (CN); Gang Su, Quzhou (CN)

(73) Assignee: Zhejiang Quhua Fluor-Chemistry Co., Ltd., Quzhou (CN)

( * ) Notice: Subject to any disclaimer, the term of this patent is extended or adjusted under 35 U.S.C. 154(b) by 0 days.

(21) Appl. No.: 14/967,242

(22) Filed: Dec. 11, 2015

(65) Prior Publication Data
US 2016/0096787 A1    Apr. 7, 2016

Related U.S. Application Data

(63) Continuation-in-part of application No. PCT/CN2014/001059, filed on Nov. 28, 2014.

(30) Foreign Application Priority Data

Aug. 8, 2014    (CN) .......................... 2014 1 0388875

(51) Int. Cl.
*C07C 17/20* (2006.01)
*C07C 17/00* (2006.01)
*C07C 17/383* (2006.01)
*C07C 21/18* (2006.01)
*C07C 17/087* (2006.01)

(52) U.S. Cl.
CPC .............. *C07C 17/20* (2013.01); *C07C 17/087* (2013.01); *C07C 17/204* (2013.01); *C07C 17/383* (2013.01); *C07C 21/18* (2013.01)

(58) Field of Classification Search
CPC .... C07C 17/20; C07C 17/204; C07C 17/383; C07C 21/18; C07C 17/087
USPC .................................................. 570/160, 161
See application file for complete search history.

(56) References Cited

U.S. PATENT DOCUMENTS 8,114,308 B2 * 2/2012 Merkel ................ A62D 1/0057
                                                          252/364

* cited by examiner

*Primary Examiner* — Jafar Parsa

(74) *Attorney, Agent, or Firm* — Matthias Scholl, PC; Matthias Scholl

(57) ABSTRACT

A method for preparing 2,3,3,3-tetrafluoropropene, including: a) heating and vaporizing hydrogen fluoride and 1,1,2,3-tetrachloropropene (TCP), and introducing hydrogen fluoride and TCP to a first reactor for reaction in the presence of an A-type catalyst to yield a first product mixture including 2,3-dichloro-3,3-difluoropropene ("HCFO-1232xf"), where the mole ratio between hydrogen fluoride and TCP is between 5:1 and 60:1, the reaction temperature is between 200 and 500° C., and the space velocity is between 200 and 2000 h$^{-1}$; b) preheating the first product mixture including HCFO-1232xf, introducing the first product mixture including HCFO-1232xf to a second reactor for reaction in the presence of a B-type catalyst to yield a second product mixture including HFO-1234yf, where the temperature of the preheated first product mixture including HCFO-1232xf is higher than the reaction temperature of the first reactor and lower than the reaction temperature of the second reactor.

5 Claims, 1 Drawing Sheet

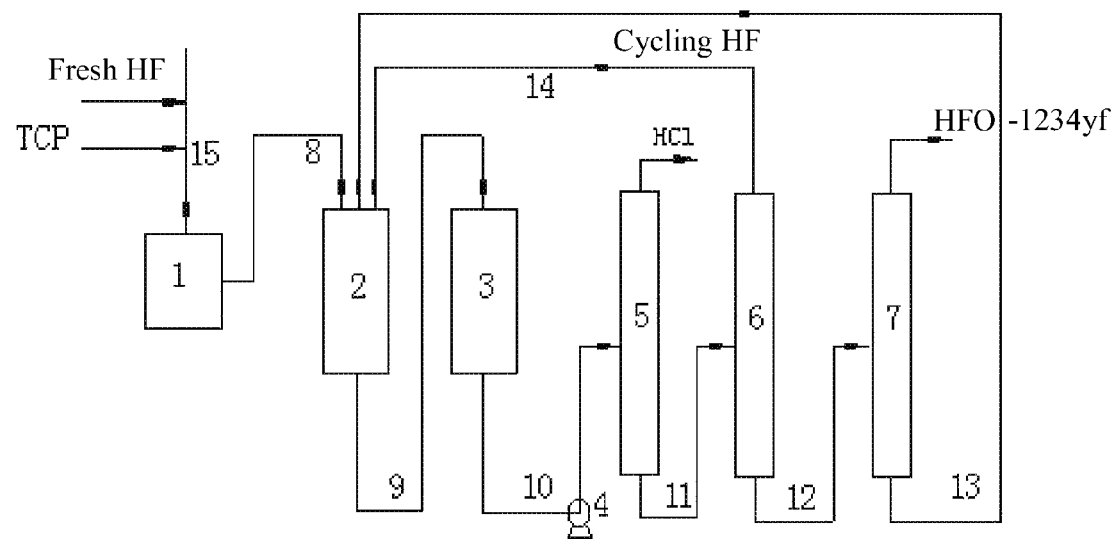

METHOD FOR PREPARING 2,3,3,3-TETRAFLUOROPROPENE

CROSS-REFERENCE TO RELATED APPLICATIONS

This application is a continuation-in-part of International Patent Application No. PCT/CN2014/001059 with an international filing date of Nov. 28, 2014, designating the United States, now pending, and further claims priority benefits to Chinese Patent Application No. 201410388875.3 filed Aug. 8, 2014. The contents of all of the aforementioned applications, including any intervening amendments thereto, are incorporated herein by reference. Inquiries from the public to applicants or assignees concerning this document or the related applications should be directed to: Matthias Scholl P.C., Attn.: Dr. Matthias Scholl Esq., 245 First Street, 18th Floor, Cambridge, Mass. 02142.

BACKGROUND OF THE INVENTION

1. Field of the Invention

The invention relates to a method for preparing 2,3,3,3-tetrafluoropropene ("HFO 1234yf").

2. Description of the Related Art

A typical method for preparing HFO-1234yf often involves long synthesis, low catalytic conversion rate, high energy consumption, high corrosion of equipment, relatively large amount of byproducts, and low yield.

SUMMARY OF THE INVENTION

In view of the above-described problems, it is one objective of the invention to provide a method for preparing HFO-1234yf that is relatively simple, features moderate reaction condition, high yield, and good product selectivity, and produces only a small amount of byproducts.

To achieve the above objective, in accordance with one embodiment of the invention, there is provided a method for preparing HFO-1234yf. The method comprises:

a) heating and vaporizing hydrogen fluoride and 1,1,2,3-tetrachloropropene (TCP), and introducing hydrogen fluoride and TCP to a first reactor for reaction in the presence of an A-type catalyst whereby yielding a first product mixture comprising 2,3-dichloro-3,3-difluoropropene, where a mole ratio between hydrogen fluoride and TCP is between 5:1 and 60:1, a reaction temperature is between 200 and 500° C., and a space velocity is between 200 and 2000 $h^{-1}$;

b) preheating the first product mixture comprising 2,3-dichloro-3,3-difluoropropene (HCFO-1232xf), introducing the first product mixture comprising HCFO-1232xf to a second reactor for reaction in the presence of a B-type catalyst, whereby yielding a second product mixture comprising HFO 1234yf, where the reaction temperature of the second reactor is higher than the reaction temperature of the first reactor by between 30 and 180° C., and the temperature of the preheated first product mixture comprising HCFO-1232xf is higher than the reaction temperature of the first reactor and lower than the reaction temperature of the second reactor;

c) introducing the second product mixture comprising HFO-1234yf to a first distillation column for a first distillation to separate a first distillate from first bottom components, and refining the first distillate to obtain hydrochloric acid;

d) introducing the first bottom components to a second distillation column for a second distillation to separate a second distillate from second bottom components, and circulating the second distillate to the first reactor, in which the second distillate is HF; and e) introducing the second bottom components to a third distillation column for a third distillation to separate a third distillate from third bottom components, collecting the third distillate to obtain HFO-1234yf, and circulating the third bottom components to the first reactor.

In a class of this embodiment, the mole ratio of the hydrogen fluoride and TCP in a) is between 10:1 and 40:1, the reaction temperature is between 230 and 450° C., and the space velocity is between 500 and 1000 $h^{-1}$.

In a class of this embodiment, the A-type catalyst in a) comprises: between 82 and 99 wt. % of chromium oxide, between 0.5 and 16 wt. % of alumina, and between 0.1 and 2.5 wt. % of waterglass.

In a class of this embodiment, in b), the reaction temperature in the second reactor is higher than the reaction temperature of the first reactor by between 50 and 150° C.

In a class of this embodiment, the B-type catalyst in a) comprises: between 93.8 and 99.8 wt. % of chromium oxide, and between 0.2 and 6.2 wt. % of indium oxide or gallium oxide.

The first product mixture is produced from the reaction between the hydrogen fluoride and TCP in the first reactor and comprises: HCFO-1232xf, HCFO-1233xf, 2-chloro-1,1,1,2-tetrafluoropropane (HCFC-244bb), 1,1,1,2,2-pentafluoropropane (HFC-245cb), hydrogen chloride, HFO-1234yf, and unreacted 1,1,2,3-tetrachloropropene and hydrogen fluoride. The first product mixture is directly introduced from the first reactor to the second reactor for reaction. Materials from an outlet of the second reactor is fed into the first distillation column to separate hydrogen chloride, and the first bottom components of the first distillation column is fed into the second distillation column for carrying out the second distillation, so that the second bottom components and the second distillate are yielded. The second distillate is HF which is circulated to the first reactor.

The second bottom components comprise: HFO-1234yf, HCFO-1232xf, HF, HCl, HCFC 244bb, and HFC-245cb. The second bottom components are fed into the third distillation column for carrying out the third distillation and yielding the third bottom components and the third distillate. The third bottom components comprise: unreacted HCFO-1232xf, HCFO-1233xf, HCFC-244bb, and HFC-245cb. The third bottom components are then circulated to the second reactor, and the collected third distillate is the HFO-1234yf.

In a), because TCP is an olefin, when the reaction temperature is too high, the fluorination of HCFO-1232xf is continued to form a large amount of HCFO-1233xf, much byproduct is produced in the reaction, the carbon formation velocity of the catalyst increases, leading to the deactivation of the catalyst. When the reaction temperature is too low, the conversion rate of TCP is not high, the unreacted TCP is continuously circulated to the reactor, and the energy consumption is increased. Thus, the reaction temperature of a) is between 200 and 500° C., and preferably between 230 and 450° C. When the space velocity is too low, the retention time of the reactive materials in the reactor is too long, so that the HCFO-1233xf, HCFC-244bb, and HFC-245cb are produced, and the selectivity of HCFO-1232xf is not high. When the space velocity is too high, the load of the reactor is relatively small in the industrialization process, the production of the unit catalyst is lowered, thus, the space velocity of the invention is controlled at between 200 and 2000 $h^{-1}$, and preferably at between 500 and 1000 h$^{-1}$. The reaction between TCP and hydrogen fluoride is a violent exothermic reaction, and too high the temperature in local hot spots easily induces the sintering of the catalyst and the decrease of the specific area of the catalyst, which therefore leads to the deactivation of the catalyst. The hot spots of the reaction are controlled by regulating the mole ratio of TCP to hydrogen fluoride in the general industrial production process for the purpose of enabling the overdose of the hydrogen fluoride to carry away the heat quantity. However, the energy consumption is increased when the mole ratio of TCP to hydrogen fluoride is too large. In contrast, in condition of a small mole ratio, the reaction proceeds in the direction of the production of HCFO-1233xf. Thus, the mole ratio of TCP to hydrogen fluoride is between 5:1 and 60:1, and preferably between 10:1 and 40:1.

When the reaction temperature in the second reactor of b) is too low, the one-way conversion of HCFO-1232xf is low, contents of HCFO-1233xf, HCFC-244bb, and HFC 245cb increase, and the reaction is difficult to proceed towards the direction of HFO 1234yf. When the reaction temperature in too high, the activity of the catalyst is improved, the content of HFO-1234yf increases, however, the carbon formation seriously occurs on the catalyst, the service life of the catalyst is shortened, which is not beneficial for the industrial production. After exploring the best balanced system of HCFO-1233xf, HCFC-244bb, HFC-245cb, and HFO-1234yf under different work conditions of the catalyst, the reaction temperature of the second reactor is between 30 and 180° C. higher than that of the first reactor, and preferably between 50 and 150° C.

Catalyst containing chromium oxide known in the technical field is adopted in a). The method for preparing the catalyst comprises: thermally decomposing a raw material, ammonium bichromate, at a certain temperature to yield chromium oxide, drying and calcining chromium oxide to obtain powder particles, adding alumina and an additive to the powder particles, shaping by pressing a resulting mixture to produce a catalyst precursor in a column shape, and fluorinating the catalyst precursor to yield the fluorinated catalyst. The catalyst prepared by the thermal decomposition has large specific area, uniform particles, and high repeatability. Besides, the addition of the alumina is adapted to improve the surface acidity of the catalyst and the selectively of the objective product HCFO-1232xf. The catalyst of a) preferably comprises: between 82 and 99 wt. % of chromium oxide, between 0.5 and 16 wt. % of alumina, and between 0.1 and 2.5 wt. % of the waterglass.

The catalyst of b) adopts chromium oxide as the main component and a metal component as an auxiliary component. The auxiliary component is preferably indium or gallium. A method for preparing the catalyst comprises: thermally decomposing a raw material, ammonium bichromate, at a certain temperature to yield chromium oxide, drying and calcining chromium oxide to obtain power particles; preparing a solution containing a indium salt or a gallium salt, impregnating the solution into the particles of chromium oxide, drying, calcining, and shaping by pressing so as to obtain a catalyst precursor in the column shape, and fluorinating the catalyst precursor to yield the fluorinated catalyst. The addition of indium or gallium is able to enhance the driving force of the reaction, improve the catalyst activity, and decrease the carbon formation on the surface of the catalyst. The catalyst of b) comprises: between 93.8 and 99.8 wt. % of chromium oxide, and between 0.2 and 6.2 wt. % of indium oxide or gallium oxide.

The activity of the catalyst gradually decreases after a certain duration of the reaction and can be recovered by regeneration means. 1,1,2,3-tetrachloropropene and hydrogen fluoride are reacted to form HCFO-1232xf. Because the olefin is easily attached to the catalyst surface to form a coking layer and result in intoxication of the catalyst, the specific area of the catalyst is quickly decreased, which is not beneficial for the F/Cl exchange reaction in thermodynamics. HCFO-1232xf and hydrogen fluoride are reacted at a higher temperature to produce HFO-1234yf, during which carbon formation occurs in a small amount of HCFO-1232xf and the micropores of the catalyst are obstructed. Moreover, the high temperature facilitates the coking of the catalyst. Thus, the catalyst is deactivated due to the structure variation. The regeneration method of the catalyst is that compressed air generally at the temperature of between 350 and 450° C., which is higher than the reaction temperature, is introduced. The high the temperature is, the complete the burning of the carbon is, but the mechanical strength of the catalyst is decreased and the service life of the catalyst is shortened. The main component of the catalyst is chromium oxide. At the same time the compressed air is introduced to burn the carbon, a small amount of $Cr^{3+}$ in the chromium oxide is transformed into $Cr^{6+}$. As being easily dissolved in water, $Cr^{6+}$ is prone to be lost, thereby resulting in the decrease of the chromium content in the catalyst. Generally, hydrogen reduction is adopted to reduce $Cr^{6+}$ into $Cr^{3+}$. The heat quantity in the regeneration process is controlled by controlling the volume of the compressed air, and the regeneration process is conducted in the fluorination reactor.

The reaction can be performed in any reactors suitable for the gas phase fluorination reaction. Preferably, the reactor is made of materials, such as Hastally and Inconel, that is anticorrosive to hydrogen fluoride and the catalyst. During the gas phase process, the reactor is filled with the gas phase fluorinated catalyst, and different shapes of the catalyst can be selected according to the reactor, and preferably, the catalyst is shaped by pressing. The flow direction of the materials in the reactor is determined by reasonably selecting the height and the diameter of the catalyst bed. Columns having a specification of φ3×3 are filled into the reactor to ensure the uniform porosity. The size of the catalyst particle may result in dispersion of the gas mixture along the axial and the radial directions, or even occurrence of channeling, which prevents the gas mixture from passing the cross-section of the catalyst bed at a uniform speed. As the size of the catalyst particle is determined, the height and the diameter of the catalyst bed of the reactor is properly selected according that the proper value of the diameter of the catalyst particle is at least 10 times smaller than the diameter of the reaction tube and is 100 times smaller than the length of the catalyst bed to satisfy the requirement of the plug flow reactor.

In order to eliminate the wall effect and to prevent the catalyst bed from being too hot, a ratio of the diameter of the reactor dr to the diameter dg of the particle of the catalyst is larger than 10, thereby eliminating the wall effect. For those reactions having not so small thermal reaction, when the ratio is larger than 12, problem of the thermal dissipation occurs in the catalyst bed. According to quantities of practical experiences, the cross section of the reaction tube is generally required to accommodate between 6 and 12 catalyst particles in parallel. The height of the catalyst bed is required to be larger than the diameter by between 2.5 and 3 times.

In the first reactor, hydrogen fluoride and TCP are reacted to form the first product mixture comprising HCFO-1232xf. The first product mixture output from the outlet of the first reactor is then preheated and then introduced to the second reactor for reaction and therefore the second product mixture comprising HFO-1234yf is produced. The second product mixture specifically comprises: the product HFO-1234yf, unreacted HCFO-1232xf, unreacted HF, HCl, HCFC-244bb, and HFC-245cb, which are separated in the subsequent systems.

Separation of HCl:

The first distillation column is adapted to remove HCL from the mixed products, HCl of high purity is separated out from the top of the distillation column and then absorbed by a deionized water to prepare hydrochloric acid of different concentrations as a by-product. The remaining bottom components are discharged from the bottom of the first distillation column and introduced to the second distillation column as the first intermediate materials after purification.

Separation of HF and Rectification of Product:

HF is separated from a top of the second distillation column, and the second bottom components comprising HFO-1234yf, HCFO-1232xf, HF and HCl, HCFC-244bb, and HFC-245cb are introduced into the third distillation column where HFO-1234yf is separated out from the top thereof, and the third bottom components in the third distillation column comprising HCFO-1232xf and HCFC-244bb and HFC-245cb are returned to the first reactor for continuing the reaction.

Advantages of the method for preparing HFO-1234yf according to embodiments of the invention are summarized as follows:

1. The method of the invention has simple process flow and low production cost. By regulating the mole ratio of the anhydrous hydrogen fluoride to TCP and epitomizing parameters including the reaction temperature and the space velocity, the conversion rate of TCP basically reaches 100 wt. %, so that the products from the first reactor are almost not required to separate the unreacted TCP, and the separating device is not necessary. The method features simple process, low energy consumption, and small investment in devices.

2. The method of the invention is environment protective and few three wastes are produced. The adoption of the gas-liquid catalytic reaction produces much less three wastes than the liquid phase route, and the reaction condition is moderate.

3. The yield of the method is high, and the selectivity is good. The yield of HFO 1234f is generally 50.3 wt. % and a maximum yield thereof may reach 61.3 wt. %.

BRIEF DESCRIPTION OF THE DRAWINGS

The invention is described hereinbelow with reference to accompanying drawings, in which the sole FIGURE is flow chart showing a method for preparing HFO-1234yf according to one embodiment of the invention.

In the drawings, the following reference numbers are used: 1. Vaporizer; 2. First reactor; 3. Second reactor; 4. Compression pump; 5. First distillation column; 2. Second distillation column; 7. Third distillation column; and 8-15. Pipelines.

DETAILED DESCRIPTION OF THE EMBODIMENTS

For further illustrating the invention, experiments detailing a method for preparing HFO-1234yf are described below. It should be noted that the following examples are intended to describe and not to limit the invention.

As shown in the flow chart of the sole FIGURE, fresh AHF and TCP were introduced via a first pipeline 15 to a vaporizer 1 where the AHF and the TCP were heated and vaporized. The vaporized AHF and TCP were introduced via a second pipeline 8 to a first reactor 2 containing an A-type catalyst for carrying out reaction. A first product mixture comprising HCFO-1232xf, HCFO-1233xf, HFO-1234yf, HF, and HCl was then fed to a second reactor 3 containing a B-type catalyst via a third pipeline 9. Thereafter, a second product mixture comprising HFO-1234yf, HCFO-1232xf, HF, HCl, HCFC-244bb, and HFC-245cb was discharged from an outlet of the second reactor 3, and transported via a fourth pipeline 10 to a compression pump 4 where the second product mixture was then compressed. The second product mixture after compression entered a first distillation tower 5 for separating HCl by dry fractionation. HCl was separated from a top of the distillation tower 5 and was thereafter refined to yield hydrochloric acid. First bottom components in the first distillation column 5 were introduced via a fifth pipeline 11 to a second distillation column 6 where HF was separated from a top thereof and returned to the first reactor 2 via a sixth pipeline 14. After that, second bottom components of the second distillation column 6 were transported via a seventh pipeline 12 to a third distillation column 7 where HFO-1234yf was then separated from a top thereof. Thereafter, third bottom components of the third distillation column 7 comprising HCFO 1232xf, HCFO-1233xf, HCFC-244bb, and HFC-245cb were circulated via an eighth pipeline 13 to the first reactor 2 for continuing the reaction therein.

Example 1

150 mL of the A-type catalyst was added to the first reactor, and 150 mL of the B-type catalyst was added to the second reactor. The A-type catalyst comprised: 98 wt. % of chromium oxide, 1.5 wt. % of alumina, and 0.5 wt. % of waterglass. The A-type catalyst was shaped by pressing into φ4×4 to form a first catalyst precursor. The B-type catalyst comprised: 99 wt. % of chromium oxide and 1 wt. % of indium oxide. The B-type catalyst was shaped by pressing into φ3×3 to form a second catalyst precursor.

The temperature of the first reactor was increased to 350° C. at different heating rats in three sections, that is, 1° C./min from the room temperature to 150° C., 0.5° C./min from 150 to 300° C., and 0.2° C./min from 300 to 350° C. Then, nitrogen gas was introduced to the first reactor at a flow rate of 2.5 L/h for drying for 6 hrs, and the temperature was decreased to 260° C. after drying. 90 vol. % of the nitrogen gas and 10 vol. % of anhydrous hydrogen fluoride were introduced for activation treatment. As hydrogen fluoride was firstly introduced, the hot spots of the reactor bed were relatively obvious, and the hot spots of the catalyst bed were controlled to be no exceeding 380° C. by the volume of the nitrogen gas. After the hot spots of the reaction tended to be stable, the temperature was increased to 350° C., the volume of the nitrogen gas was gradually decreased until the nitrogen gas is turned off, and the activation was then activated. The volume of the produced water at the outlet of the reactor was analyzed every four hrs. The water production was smaller than 1 g/hr, the activation of the A-type catalyst was then accomplished. The whole activation process lasted approximately 96 hrs.

The activation of the B-type catalyst was the same as that of the A-type catalyst.

The temperature of the bed of the first reactor was regulated to 250° C., and the temperature of the bed of the second reactor was regulated to 330° C. Thereafter, materials were fed for carrying out the reaction. TCP and hydrogen fluoride were mixed and introduced to the gasifier. A mole ratio between HF and TCP was 20:1, and a space velocity was between 500 h$^{-1}$. A first product mixture comprising HCFO-1232xf output from an outlet of the first reactor was preheated to 315° C. and then introduced to the second reactor. A second product mixture output from an outlet of the second reactor was then treated by the first distillation column, the second distillation column, and the third distillation column, successively. A product HFO-1234yf was finally yielded, and a purity thereof was 99.9 wt. %. The product mixtures collected respectively at the outlet of the first reactor and the outlet of the second reactor were analyzed after washed by an alkali, and organic components thereof were listed in Table 1:

TABLE 1

| Component | HFO-1234yf | HCFO-1232xf | HCFO-1233xf | HCFC-244bb | HFC-245cb |
|---|---|---|---|---|---|
| First reactor | 0.5 wt. % | 90.6 wt. % | 8.5 wt. % | 0.2 wt. % | 0.2 wt. % |
| Second reactor | 50.3 wt. % | 24.6 wt. % | 24.2 wt. % | 0.4 wt. % | 0.5 wt. % |

Example 2

150 mL of the A-type catalyst was added to the first reactor, and 150 mL of the B-type catalyst was added to the second reactor. The A-type catalyst comprised: 99 wt. % of chromium oxide, 0.7 wt. % of alumina, and 0.3 wt. % of waterglass. The A-type catalyst was shaped by pressing into ϕ4×4 to form a first catalyst precursor. The B-type catalyst comprised: 98 wt. % of chromium oxide and 2 wt. % of indium oxide. The B-type catalyst was shaped by pressing into ϕ3×3 to form a second catalyst precursor. Activations of the A-type catalyst and the B-type catalyst were the same as that of Example 1.

The temperature of the bed of the first reactor was regulated to 240° C., and the temperature of the bed of the second reactor was regulated to 350° C. Thereafter, materials were fed for carrying out the reaction. TCP and hydrogen fluoride were mixed and introduced to the gasifier. A mole ratio between HF and TCP was 15:1, and a space velocity was between 500 $h^{-1}$. A first product mixture comprising HCFO-1232xf output from an outlet of the first reactor was preheated to 310° C. and then introduced to the second reactor. A second product mixture output from an outlet of the second reactor was then treated by the first distillation column, the second distillation column, and the third distillation column, successively. A product HFO-1234yf was finally yielded, and a purity thereof was 99.9 wt. %. The product mixtures collected respectively at the outlet of the first reactor and the outlet of the second reactor were analyzed after washed by an alkali, and organic components thereof were listed in Table 2:

TABLE 2

| Component | HFO-1234yf | HCFO-1232xf | HCFO-1233xf | HCFC-244bb | HFC-245cb |
|---|---|---|---|---|---|
| First reactor | 0.2 wt. % | 91.4 wt. % | 8.1 wt. % | 0.2 wt. % | 0.1 wt. % |
| Second reactor | 52.4 wt. % | 22.8 wt. % | 24.0 wt. % | 0.6 wt. % | 0.2 wt. % |

Example 3

150 mL of the A-type catalyst was added to the first reactor, and 150 mL of the B-type catalyst was added to the second reactor. The A-type catalyst comprised: 96 wt. % of chromium oxide, 3.2 wt. % of alumina, and 0.8 wt. % of waterglass. The A-type catalyst was shaped by pressing into ϕ4×4 to form a first catalyst precursor. The B-type catalyst comprised: 97 wt. % of chromium oxide and 3 wt. % of indium oxide. The B-type catalyst was shaped by pressing into ϕ3×3 to form a second catalyst precursor. Activations of the A-type catalyst and the B-type catalyst were the same as that of Example 1.

The temperature of the bed of the first reactor was regulated to 260° C., and the temperature of the bed of the second reactor was regulated to 360° C. Thereafter, materials were fed for carrying out the reaction. TCP and hydrogen fluoride were mixed and introduced to the gasifier. A mole ratio between HF and TCP was 25:1, and a space velocity was between 1000 $h^{-1}$. A first product mixture comprising HCFO-1232xf output from an outlet of the first reactor was preheated to 320° C. and then introduced to the second reactor. A second product mixture output from an outlet of the second reactor was then treated by the first distillation column, the second distillation column, and the third distillation column, successively. A product HFO-1234yf was finally yielded, and a purity thereof was 99.9 wt. %. The product mixtures collected respectively at the outlet of the first reactor and the outlet of the second reactor were analyzed after washed by an alkali, and organic components thereof were listed in Table 3:

TABLE 3

| Component | HFO-1234yf | HCFO-1232xf | HCFO-1233xf | HCFC-244bb | HFC-245cb |
|---|---|---|---|---|---|
| First reactor | 0.1 wt. % | 89.5 wt. % | 10.2 wt. % | 0.1 wt. % | 0.1 wt. % |
| Second reactor | 56.5 wt. % | 20.3 wt. % | 23.1 wt. % | 0.1 wt. % | 0 |

Example 4

150 mL of the A-type catalyst was added to the first reactor, and 150 mL of the B-type catalyst was added to the second reactor. The A-type catalyst comprised: 90 wt. % of chromium oxide, 9 wt. % of alumina, and 1 wt. % of waterglass. The A-type catalyst was shaped by pressing into ϕ4×4 to form a first catalyst precursor. The B-type catalyst comprised: 96.6 wt. % of chromium oxide and 3.4 wt. % of indium oxide. The B-type catalyst was shaped by pressing into ϕ3×3 to form a second catalyst precursor. Activations of the A-type catalyst and the B-type catalyst were the same as that of Example 1.

The temperature of the bed of the first reactor was regulated to 280° C., and the temperature of the bed of the second reactor was regulated to 340° C. Thereafter, materials were fed for carrying out the reaction. TCP and hydrogen fluoride were mixed and introduced to the gasifier. A mole ratio between HF and TCP was 25:1, and a space velocity was between 800 h$^{-1}$. A first product mixture comprising HCFO-1232xf output from an outlet of the first reactor was preheated to 330° C. and then introduced to the second reactor. A second product mixture output from an outlet of the second reactor was then treated by the first distillation column, the second distillation column, and the third distillation column, successively. A product HFO-1234yf was finally yielded, and a purity thereof was 99.9 wt. %. The product mixtures collected respectively at the outlet of the first reactor and the outlet of the second reactor were analyzed after washed by an alkali, and organic components thereof were listed in Table 4:

TABLE 4

| Component | HFO-1234yf | HCFO-1232xf | HCFO-1233xf | HCFC-244bb | HFC-245cb |
|---|---|---|---|---|---|
| First reactor | 0.5 wt. % | 90.3 wt. % | 8.6 wt. % | 0.4 wt. % | 0.2 wt. % |
| Second reactor | 51.8 wt. % | 21.6 wt. % | 26.0 wt. % | 0.3 wt. % | 0.3 wt. % |

Example 5

150 mL of the A-type catalyst was added to the first reactor, and 150 mL of the B-type catalyst was added to the second reactor. The A-type catalyst comprised: 92.6 wt. % of chromium oxide, 5.3 wt. % of alumina, and 2.1 wt. % of waterglass. The A-type catalyst was shaped by pressing into φ4×4 to form a first catalyst precursor. The B-type catalyst comprised: 97.8 wt. % of chromium oxide and 2.2 wt. % of gallium oxide. The B-type catalyst was shaped by pressing into φ3×3 to form a second catalyst precursor. Activations of the A-type catalyst and the B-type catalyst were the same as that of Example 1.

The temperature of the bed of the first reactor was regulated to 230° C., and the temperature of the bed of the second reactor was regulated to 380° C. Thereafter, materials were fed for carrying out the reaction. TCP and hydrogen fluoride were mixed and introduced to the gasifier. A mole ratio between HF and TCP was 25:1, and a space velocity was between 600 h$^{-1}$. A first product mixture comprising HCFO-1232xf output from an outlet of the first reactor was preheated to 340° C. and then introduced to the second reactor. A second product mixture output from an outlet of the second reactor was then treated by the first distillation column, the second distillation column, and the third distillation column, successively. A product HFO-1234yf was finally yielded, and a purity thereof was 99.9 wt. %. The product mixtures collected respectively at the outlet of the first reactor and the outlet of the second reactor were analyzed after washed by an alkali, and organic components thereof were listed in Table 5:

TABLE 5

| Component | HFO-1234yf | HCFO-1232xf | HCFO-1233xf | HCFC-244bb | HFC-245cb |
|---|---|---|---|---|---|
| First reactor | 0.1 wt. % | 93.2 wt. % | 6.1 wt. % | 0.4 wt. % | 0.2 wt. % |
| Second reactor | 55.5 wt. % | 37.3 wt. % | 6.7 wt. % | 0.4 wt. % | 0.1 wt. % |

Example 6

150 mL of the A-type catalyst was added to the first reactor, and 150 mL of the B-type catalyst was added to the second reactor. The A-type catalyst comprised: 95.9 wt. % of chromium oxide, 2.8 wt. % of alumina, and 1.3 wt. % of waterglass. The A-type catalyst was shaped by pressing into φ4×4 to form a first catalyst precursor. The B-type catalyst comprised: 98.5 wt. % of chromium oxide and 1.5 wt. % of gallium oxide. The B-type catalyst was shaped by pressing into φ3×3 to form a second catalyst precursor. Activations of the A-type catalyst and the B-type catalyst were the same as that of Example 1.

The temperature of the bed of the first reactor was regulated to 250° C., and the temperature of the bed of the second reactor was regulated to 350° C. Thereafter, materials were fed for carrying out the reaction. TCP and hydrogen fluoride were mixed and introduced to the gasifier. A mole ratio between HF and TCP was 25:1, and a space velocity was between 500 h$^{-1}$. A first product mixture comprising HCFO-1232xf output from an outlet of the first reactor was preheated to 340° C. and then introduced to the second reactor. A second product mixture output from an outlet of the second reactor was then treated by the first distillation column, the second distillation column, and the third distillation column, successively. A product HFO-1234yf was finally yielded, and a purity thereof was 99.9 wt. %. The product mixtures collected respectively at the outlet of the first reactor and the outlet of the second reactor were analyzed after washed by an alkali, and organic components thereof were listed in Table 6:

TABLE 6

| Component | HFO-1234yf | HCFO-1232xf | HCFO-1233xf | HCFC-244bb | HFC-245cb |
|---|---|---|---|---|---|
| First reactor | 0.1 wt. % | 93.2 wt. % | 6.1 wt. % | 0.4 wt. % | 0.2 wt. % |
| Second reactor | 53.2 wt. % | 37.3 wt. % | 8.8 wt. % | 0.4 wt. % | 0.3 wt. % |

Example 7

150 mL of the A-type catalyst was added to the first reactor, and 150 mL of the B-type catalyst was added to the second reactor. The A-type catalyst comprised: 82.3 wt. % of chromium oxide, 15.8 wt. % of alumina, and 1.9 wt. % of waterglass. The A-type catalyst was shaped by pressing into φ4×4 to form a first catalyst precursor. The B-type catalyst comprised: 93.8 wt. % of chromium oxide and 6.2 wt. % of gallium oxide. The B-type catalyst was shaped by pressing into φ3×3 to form a second catalyst precursor. Activations of the A-type catalyst and the B-type catalyst were the same as that of Example 1.

The temperature of the bed of the first reactor was regulated to 300° C., and the temperature of the bed of the second reactor was regulated to 380° C. Thereafter, materials were fed for carrying out the reaction. TCP and hydrogen fluoride were mixed and introduced to the gasifier. A mole ratio between HF and TCP was 40:1, and a space velocity was between 1000 h$^{-1}$. A first product mixture comprising HCFO-1232xf output from an outlet of the first reactor was preheated to 370° C. and then introduced to the second reactor. A second product mixture output from an outlet of the second reactor was then treated by the first distillation column, the second distillation column, and the third distillation column, successively. A product HFO-1234yf was finally yielded, and a purity thereof was 99.9 wt. %. The product mixtures collected respectively at the outlet of the first reactor and the outlet of the second reactor were analyzed after washed by an alkali, and organic components thereof were listed in Table 7:

TABLE 7

| Component | HFO-1234yf | HCFO-1232xf | HCFO-1233xf | HCFC-244bb | HFC-245cb |
|---|---|---|---|---|---|
| First reactor | 1.3 wt. % | 75.6 wt. % | 21.3 wt. % | 1.0 wt. % | 0.8 wt. % |
| Second reactor | 54.2 wt. % | 35.3 wt. % | 8.6 wt. % | 1.2 wt. % | 0.7 wt. % |

Example 8

150 mL of the A-type catalyst was added to the first reactor, and 150 mL of the B-type catalyst was added to the second reactor. The A-type catalyst comprised: 88.7 wt. % of chromium oxide, 10.3 wt. % of alumina, and 1.0 wt. % of waterglass. The A-type catalyst was shaped by pressing into φ4×4 to form a first catalyst precursor. The B-type catalyst comprised: 99.8 wt. % of chromium oxide and 0.2 wt. % of gallium oxide. The B-type catalyst was shaped by pressing into φ3×3 to form a second catalyst precursor. Activations of the A-type catalyst and the B-type catalyst were the same as that of Example 1.

The temperature of the bed of the first reactor was regulated to 320° C., and the temperature of the bed of the second reactor was regulated to 400° C. Thereafter, materials were fed for carrying out the reaction. TCP and hydrogen fluoride were mixed and introduced to the gasifier. A mole ratio between HF and TCP was 30:1, and a space velocity was between 1500 h$^{-1}$. A first product mixture comprising HCFO-1232xf output from an outlet of the first reactor was preheated to 390° C. and then introduced to the second reactor. A second product mixture output from an outlet of the second reactor was then treated by the first distillation column, the second distillation column, and the third distillation column, successively. A product HFO-1234yf was finally yielded, and a purity thereof was 99.9 wt. %. The product mixtures collected respectively at the outlet of the first reactor and the outlet of the second reactor were analyzed after washed by an alkali, and organic components thereof were listed in Table 8:

TABLE 8

| Component | HFO-1234yf | HCFO-1232xf | HCFO-1233xf | HCFC-244bb | HFC-245cb |
|---|---|---|---|---|---|
| First reactor | 1.2 wt. % | 73.4 wt. % | 24.5 wt. % | 0.4 wt. % | 0.5 wt. % |
| Second reactor | 56.4 wt. % | 32.8 wt. % | 9.1 wt. % | 1.3 wt. % | 0.4 wt. % |

Example 9

150 mL of the A-type catalyst was added to the first reactor, and 150 mL of the B-type catalyst was added to the second reactor. The A-type catalyst comprised: 91.8 wt. % of chromium oxide, 6.2 wt. % of alumina, and 2.0 wt. % of waterglass. The A-type catalyst was shaped by pressing into φ4×4 to form a first catalyst precursor. The B-type catalyst comprised: 99.8 wt. % of chromium oxide and 0.2 wt. % of gallium oxide. The B-type catalyst was shaped by pressing into φ3×3 to form a second catalyst precursor. Activations of the A-type catalyst and the B-type catalyst were the same as that of Example 1.

The temperature of the bed of the first reactor was regulated to 280° C., and the temperature of the bed of the second reactor was regulated to 420° C. Thereafter, materials were fed for carrying out the reaction. TCP and hydrogen fluoride were mixed and introduced to the gasifier. A mole ratio between HF and TCP was 10:1, and a space velocity was between 2000 h$^{-1}$. A first product mixture comprising HCFO-1232xf output from an outlet of the first reactor was preheated to 370° C. and then introduced to the second reactor. A second product mixture output from an outlet of the second reactor was then treated by the first distillation column, the second distillation column, and the third distillation column, successively. A product HFO-1234yf was finally yielded, and a purity thereof was 99.9 wt. %. The product mixtures collected respectively at the outlet of the first reactor and the outlet of the second reactor were analyzed after washed by an alkali, and organic components thereof were listed in Table 9:

TABLE 9

| Component | HFO-1234yf | HCFO-1232xf | HCFO-1233xf | HCFC-244bb | HFC-245cb |
|---|---|---|---|---|---|
| First reactor | 0.1 wt. % | 65.5 wt. % | 33.6 wt. % | 0.3 wt. % | 0.5 wt. % |
| Second reactor | 58.3 wt. % | 19.8 wt. % | 21.3 wt. % | 0.5 wt. % | 0.1 wt. % |

Example 10

150 mL of the A-type catalyst was added to the first reactor, and 150 mL of the B-type catalyst was added to the second reactor. The A-type catalyst comprised: 91.8 wt. % of chromium oxide, 6.2 wt. % of alumina, and 2.0 wt. % of waterglass. The A-type catalyst was shaped by pressing into φ4×4 to form a first catalyst precursor. The B-type catalyst comprised: 99.8 wt. % of chromium oxide and 0.2 wt. % of gallium oxide. The B-type catalyst was shaped by pressing into φ3×3 to form a second catalyst precursor. Activations of the A-type catalyst and the B-type catalyst were the same as that of Example 1.

The temperature of the bed of the first reactor was regulated to 450° C., and the temperature of the bed of the second reactor was regulated to 500° C. Thereafter, materials were fed for carrying out the reaction. TCP and hydrogen fluoride were mixed and introduced to the gasifier. A mole ratio between HF and TCP was 60:1, and a space velocity was between 200 $h^{-1}$. A first product mixture comprising HCFO-1232xf output from an outlet of the first reactor was preheated to 480° C. and then introduced to the second reactor. A second product mixture output from an outlet of the second reactor was then treated by the first distillation column, the second distillation column, and the third distillation column, successively. A product HFO-1234yf was finally yielded, and a purity thereof was 99.9 wt. %. The product mixtures collected respectively at the outlet of the first reactor and the outlet of the second reactor were analyzed after washed by an alkali, and organic components thereof were listed in Table 10:

TABLE 10

| Component | HFO-1234yf | HCFO-1232xf | HCFO-1233xf | HCFC-244bb | HFC-245cb |
|---|---|---|---|---|---|
| First reactor | 12.5 wt. % | 21.2 wt. % | 65.4 wt. % | 0.6 wt. % | 0.3 wt. % |
| Second reactor | 61.3 wt. % | 10.3 wt. % | 22.6 wt. % | 3.5 wt. % | 2.3 wt. % |

While particular embodiments of the invention have been shown and described, it will be obvious to those skilled in the art that changes and modifications may be made without departing from the invention in its broader aspects, and therefore, the aim in the appended claims is to cover all such changes and modifications as fall within the true spirit and scope of the invention.

The invention claimed is:

1. A method for preparing 2,3,3,3-tetrafluoropropene, comprising:
   a) heating and vaporizing hydrogen fluoride and 1,1,2,3-tetrachloropropene, and introducing hydrogen fluoride and TCP to a first reactor for reaction in the presence of an A-type catalyst, whereby yielding a first product mixture comprising 2,3-dichloro-3,3-difluoropropene, wherein a mole ratio between hydrogen fluoride and 1,1,2,3-tetrachloropropene is between 5:1 and 60:1, a reaction temperature is between 200 and 500° C., and a space velocity is between 200 and 2000 $h^{-1}$;
   b) preheating the first product mixture comprising 2,3-dichloro-3,3-difluoropropene, introducing the first product mixture comprising 2,3-dichloro-3,3-difluoropropene to a second reactor for reaction in the presence of a B-type catalyst, whereby yielding a second product mixture comprising 2,3,3,3-tetrafluoropropene, wherein the reaction temperature of the second reactor is higher than the reaction temperature of the first reactor by between 30 and 180° C., and the temperature of the preheated first product mixture comprising 2,3-dichloro-3,3-difluoropropene is higher than the reaction temperature of the first reactor and lower than the reaction temperature of the second reactor;
   c) introducing the second product mixture comprising 2,3,3,3-tetrafluoropropene to a first distillation column for a first distillation to separate a first distillate from first bottom components, and refining the first distillate to obtain hydrochloric acid;
   d) introducing the first bottom components to a second distillation column for a second distillation to separate a second distillate from second bottom components, and circulating the second distillate to the first reactor, in which the second distillate is HF; and
   e) introducing the second bottom components to a third distillation column for a third distillation to separate a third distillate from third bottom components, collecting the third distillate to obtain 2,3,3,3-tetrafluoropropene, and circulating the third bottom components to the first reactor.

2. The method of claim 1, wherein the mole ratio of the hydrogen fluoride and 1,1,2,3-tetrachloropropene in a) is between 10:1 and 40:1, the reaction temperature is between 230 and 450° C., and the space velocity is between 500 and 1000 $h^{-1}$.

3. The method of claim 1, wherein the A-type catalyst in a) comprises: between 82 and 99 wt. % of chromium oxide, between 0.5 and 16 wt. % of alumina, and between 0.1 and 2.5 wt. % of waterglass.

4. The method of claim 1, wherein in b), the reaction temperature in the second reactor is higher than the reaction temperature of the first reactor by between 50 and 150° C.

5. The method of claim 1, wherein the B-type catalyst in b) comprises: between 93.8 and 99.8 wt. % of chromium oxide, and between 0.2 and 6.2 wt. % of indium oxide or gallium oxide.

* * * * *